US011765500B2

(12) United States Patent
Nielsen

(10) Patent No.: US 11,765,500 B2
(45) Date of Patent: *Sep. 19, 2023

(54) METHODS AND APPARATUS FOR WEAR NOISE AUDIO SIGNATURE SUPPRESSION

(71) Applicant: The Nielsen Company (US), LLC, New York, NY (US)

(72) Inventor: Christen V. Nielsen, Dunedin, FL (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/712,971

(22) Filed: Apr. 4, 2022

(65) Prior Publication Data
US 2022/0232317 A1 Jul. 21, 2022

Related U.S. Application Data

(63) Continuation of application No. 16/558,014, filed on Aug. 30, 2019, now Pat. No. 11,297,422.

(51) Int. Cl.
*G10K 11/00* (2006.01)
*H04R 3/00* (2006.01)
*A61B 5/11* (2006.01)
*G01P 15/14* (2013.01)

(52) U.S. Cl.
CPC ............ *H04R 3/002* (2013.01); *A61B 5/1118* (2013.01); *G01P 15/14* (2013.01); *G10K 11/002* (2013.01); *H04R 2460/01* (2013.01)

(58) Field of Classification Search
CPC ... H04R 3/002; H04R 2460/01; A61B 5/1118; G01P 15/14; G10K 11/002
See application file for complete search history.

(56) References Cited

U.S. PATENT DOCUMENTS

| 9,837,101 | B2 | 12/2017 | Bilobrov |
| 11,297,422 | B1 | 4/2022 | Nielsen |
| 2009/0103744 | A1 | 4/2009 | Klinghult et al. |
| 2011/0112831 | A1 | 5/2011 | Sorensen et al. |
| 2013/0343555 | A1 | 12/2013 | Yehuday et al. |
| 2017/0372721 | A1 | 12/2017 | Jasiuk et al. |
| 2018/0322860 | A1 | 11/2018 | Fong |

FOREIGN PATENT DOCUMENTS

KR  20080059881  7/2008

OTHER PUBLICATIONS

International Searching Authority, "International Search Report and Written Opinion," issued in connection with International Patent Application No. PCT/US2020/047853, dated Nov. 25, 2020, 13 pages.

(Continued)

*Primary Examiner* — Ping Lee

(57) ABSTRACT

Methods, apparatus, systems and articles of manufacture are disclosed for wear noise audio signature suppression. An example method disclosed herein includes generating an audio signature based on a media audio signal during a first time period, collecting acceleration data during the first time period, determining whether the acceleration data corresponds to wear noise having occurred during the first time period, and in response to determining the acceleration data corresponds to wear noise during the first time period, inhibiting transmission of the audio signature to a central facility.

20 Claims, 5 Drawing Sheets

(56) References Cited

OTHER PUBLICATIONS

International Bureau, "International Preliminary Report on Patentability," issued in connection with International Patent Application No. PCT/US2020/047853, dated Mar. 1, 2022, 6 pages.

"Suggestions for Lowering Accelerometer Noise," Arduino Forum, Feb. 21-28, 2011, 4 pages.

Covell et al., "Waveprint Efficient Wavelet-Based Audio Fingerprinting," Google, Inc., vol. 41, No. 11, 2008, 3 pages.

"MEMS Accelerometer: Noise Reduction and Improve Resolution," National Instruments Discussion Forums, Mar. 10-11, 2014, 3 pages.

United States Patent and Trademark Office, "Non-Final Office Action," issued in connection with U.S. Appl. No. 16/558,014, dated Feb. 23, 2021, 7 pages.

United States Patent and Trademark Office, "Final Office Action," issued in connection with U.S. Appl. No. 16/558,014, dated Jun. 15, 2021, 9 pages.

United States Patent and Trademark Office, "Advisory Action," issued in connection with U.S. Appl. No. 16/558,014, dated Sep. 3, 2021, 3 pages.

United States Patent and Trademark Office, "Notice of Allowance and Fee(s) Due," issued in connection with U.S. Appl. No. 16/558,014, dated Aug. 26, 2020, 7 pages.

United States Patent and Trademark Office, "Notice of Allowance and Fee(s) Due," issued in connection with U.S. Appl. No. 16/558,014, dated Dec. 2, 2021, 5 pages.

METHODS AND APPARATUS FOR WEAR NOISE AUDIO SIGNATURE SUPPRESSION

RELATED APPLICATIONS

This patent arises from a continuation of U.S. application Ser. No. 16/558,014, entitled "METHODS AND APPARATUS FOR WEAR NOISE AUDIO SIGNATURE SUPPRESSION" and filed on Aug. 30, 2019, which is hereby incorporated herein by reference in its entirety.

FIELD OF THE DISCLOSURE

This disclosure relates generally to media monitoring, and, more particularly, to methods and apparatus for wear noise audio signature suppression.

BACKGROUND

Monitoring companies desire knowledge on how users interact with media and media devices such as smartphones, tablets, laptops, smart televisions, etc. In particular, media monitoring companies want to monitor media presentations made at the media devices to, among other things, monitor exposure to advertisements, determine advertisement effectiveness, determine user behavior, identify purchasing behavior associated with various demographics, etc. Media monitoring can be performed by portable devices worn by users (e.g., panelists). Some media monitoring devices include microphones to detect audio from media presentation devices (e.g., a television, a radio, a Bluetooth speaker, etc. and enable crediting of media presentations.

BRIEF DESCRIPTION OF THE DRAWINGS

In general, the same reference numbers will be used throughout the drawing(s) and accompanying written description to refer to the same or like parts.

Figure 1:
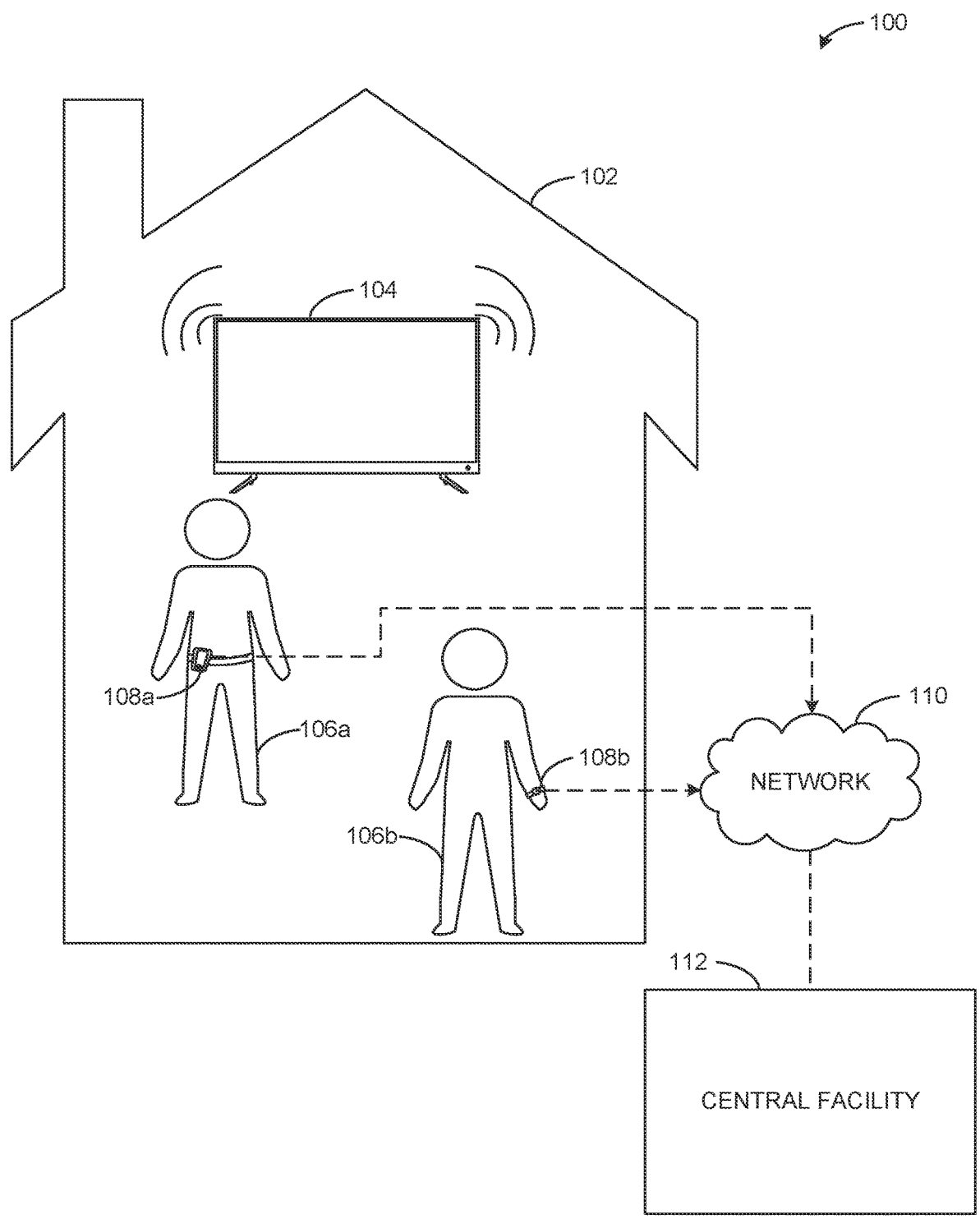
FIG. 1 is a schematic diagram of an example environment in which media monitoring is performed.

Descriptors "first," "second," "third," etc. are used herein when identifying multiple elements or components which may be referred to separately. Unless otherwise specified or understood based on their context of use, such descriptors are not intended to impute any meaning of priority, physical order or arrangement in a list, or ordering in time but are merely used as labels for referring to multiple elements or components separately for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for ease of referencing multiple elements or components.

As used herein, the term "media" includes any type of content and/or advertisement delivered via any type of distribution medium. Thus, media includes television programming or advertisements, radio programming or advertisements, movies, web sites, streaming media, etc.

DETAILED DESCRIPTION

One technique monitoring companies utilize to monitor media is to use media monitoring devices. For example, a media monitor (also referred to as a meter or media meter) may be worn by a user (e.g., as a wearable device) to either selectively (e.g., in response to being turned on, being enabled, etc.) or continuously monitor media to which the media monitor is exposed. A media monitor may include a microphone to measure audio signals corresponding to a media presentation. Media monitors which are worn on the body may be affixed to a user via the user's belt, affixed via the user's wrist (e.g., as a watch), carried as an accessory (e.g., a pendant) (e.g., worn around the neck, as part of glasses, as part of a headset, etc.), and/or to affixed to any other body party. In some examples, media monitors may be incorporated into wearable devices with other functions as well (e.g., a smart watch).

When monitoring media via a media monitor worn on a user's body, a microphone on the media monitor that is used to sense and/or record audio signals may additionally capture audio associated with noise. For example, the microphone on the media monitor may capture wear noise. As used herein, wear noise refers to audio that corresponds to noise caused by the microphone of the media monitor contacting a user and/or a user's garments (e.g., clothing, purse, accessories, etc.). For example, if a media monitor is kept in a pocket, the microphone of the media monitor may capture wear noise from the user's pants when the user is moving. Similarly, if the media monitor is worn on the wrist and the user is wearing a long-sleeve shirt, the microphone of the media monitor may capture wear noise against the sleeve of the shirt. Audio signals captured by the microphone of the media monitor when wear noise is occurring are often not usable for media identification. For example, when performing media identification based on audio signatures, even minor wear noise may result in differences in the resulting audio signatures that make media identification very difficult or impossible.

Signature-based media monitoring techniques generally use one or more inherent characteristics of the monitored media during a monitoring time interval to generate a substantially unique representation of the media. Such a representation is referred to as a signature or fingerprint, and can take any form (e.g., a series of digital values, a waveform, etc.) representative of any aspect(s) of the media signal(s) (e.g., the audio and/or video signals forming the media presentation being monitored). A signature may be a series of signatures collected in series over a timer interval. A good signature is repeatable when processing the same media presentation, but is unique relative to other (e.g., different) presentations of other (e.g., different) media. Accordingly, the term "fingerprint" and "signature" are used interchangeably herein and are defined herein to mean a proxy for identifying media that is generated from one or more inherent characteristics of the media.

Signature-based media monitoring generally involves determining (e.g., generating and/or collecting) signature(s)

representative of a media signal (e.g., an audio signal and/or a video signal) output by a monitored media device and comparing the monitored signature(s) to one or more references signatures corresponding to known (e.g., reference) media sources. Various comparison criteria, such as a cross-correlation value, a Hamming distance, etc., can be evaluated to determine whether a monitored signature matches a particular reference signature. When a match between the monitored signature and one of the reference signatures is found, the monitored media can be identified as corresponding to the particular reference media represented by the reference signature that with matched the monitored signature. Because attributes, such as an identifier of the media, a presentation time, a broadcast channel, etc., are collected for the reference signature, these attributes may then be associated with the monitored media whose monitored signature matched the reference signature. Example systems for identifying media based on codes and/or signatures are long known and were first disclosed in Thomas, U.S. Pat. No. 5,481,294, which is hereby incorporated by reference in its entirety.

Conventional media monitors capture audio continuously or at least continuously while enabled, regardless of whether a microphone of the media monitor is capturing wear noise. Performing media identification can be very processing intensive. For example, in some implementations, audio signatures are generated at the media monitor and then transmitted (e.g., via a network) to a central facility for processing (e.g., to be matched with reference signatures). This process can be expensive in utilizing processing resources on the device-side as well as bandwidth for transmission and processing resources at the central facility. Hence, when conventional media monitors capture audio corresponding to wear noise (and therefore not useful for accurate media identification), audio signatures are unnecessarily generated and transmitted, wasting resources to process audio signals that have a low probability of being identifiable.

Example methods, apparatus, and articles of manufacture disclosed herein detect wear noise at a media monitoring device and take measures to eliminate the wear noise (e.g., disable monitoring when wear noise is detected, discard audio during a time period in which wear noise is detected, prevent transmission of audio and/or data associated with the audio collected during a time period in which wear noise is detected, etc.). Example techniques disclosed herein determine a probability of wear noise occurring based on accelerometer data and, in response to the probability satisfying a threshold, inhibit generation and/or transmission of audio signatures. In some example techniques disclosed herein, audio signatures that are generated based on audio recorded at a time when wear noise is suspected (e.g., when a probability of wear noise satisfies a threshold) are discarded (e.g., removed from storage, not transmitted to a central facility for signature matching, etc.). In some example techniques disclosed herein, acceleration data is compared to historical acceleration data to determine whether the acceleration data has characteristics of past wear noise occurrences. In some example techniques disclosed herein, motion patterns for a particular user are identified based on historical accelerometer data, and the motion patterns are utilized to quickly and accurately identify wear noise.

Example methods, apparatus, and articles of manufacture disclosed herein monitor media presentations at media devices. Such media devices may include, for example, Internet-enabled televisions, personal computers, Internet-enabled mobile handsets (e.g., a smartphone), video game consoles (e.g., Xbox®, PlayStation®), tablet computers (e.g., an iPad®), digital media players (e.g., a Roku® media player, a Slingbox®, etc.), etc. In some examples, media monitoring information is aggregated to determine ownership and/or usage statistics of media devices, relative rankings of usage and/or ownership of media devices, types of uses of media devices (e.g., whether a device is used for browsing the Internet, streaming media from the Internet, etc.), and/or other types of media device information. In examples disclosed herein, monitoring information includes, but is not limited to, media identifying information (e.g., media-identifying metadata, codes, signatures, watermarks, and/or other information that may be used to identify presented media), application usage information (e.g., an identifier of an application, a time and/or duration of use of the application, a rating of the application, etc.), and/or user-identifying information (e.g., demographic information, a user identifier, a panelist identifier, a username, etc.).

FIG. 1 is a schematic diagram of an example environment 100 for media monitoring. The environment 100 includes an example household 102, an example media presentation device 104, an example first panelist 106a, an example second panelist 106b, an example first media monitor 108a, an example second media monitor 108b, an example network 110, and an example central facility 112.

The example household 102 of the illustrated example of FIG. 1 is a monitoring location. While a household is illustrated as an example monitoring location, the media monitoring techniques disclosed herein may be implemented in any environment. For example, media may be monitored at any location a panelist moves to, media may be monitored in a vehicle, media may be monitored at a theater, media may be monitored at a concert, etc.

The example media presentation device 104 of the illustrated example of FIG. 1 is a television. Any one or more media presentation devices may present media that is monitored by the first media monitor 108a and the second media monitor 108b. For example, the household 102 may include one or more televisions, gaming consoles, laptop computers, desktop computers, radios, wireless speaker systems, mobile devices, home automation devices, etc. In the illustrated example, the media presentation device 104 is presenting media including emitting audio that can be detected by the first media monitor 108a and the second media monitor 108b.

The first panelist 106a and the second panelist 106b of the illustrated example of FIG. 1 are people whose media consumption is being monitored (e.g., by an Audience Measurement Entity). People (e.g., households, organizations, etc.) register as panelists via, for example, a user interface presented on a media device (e.g., via a website). People may be recruited as panelists in additional or alternative manners such as, for example, via a telephone interview, by completing an online survey, etc. Additionally or alternatively, people may be contacted and/or enlisted to join a panel using any desired methodology (e.g., random selection, statistical selection, phone solicitations, Internet advertisements, surveys, advertisements in shopping malls, product packaging, etc.).

The first panelist 108a has an example first media monitor 108a attached at their waist. For example, the first media monitor 108a may be attached via a clip to a belt. The second panelist 108b has an example second media monitor 108b attached at their wrist. For example, the second media monitor 108b may be a watch (e.g., a smart watch). The first media monitor 108a and the second media monitor 108b are merely two possible embodiments of the media monitor 108. As used herein, any description or reference to the media monitor 108 applies equally to the first media monitor 108*a* and the second media monitor 108*b*.

The media monitor 108 of the illustrated example of FIG. 1 measures media consumption and communicates with the central facility 112. For example, the media monitor 108 can include an audio sensor (e.g., a microphone) to measure audio media signals. The media monitor 108 of the illustrated example includes an accelerometer to determine whether characteristics of motion of the media monitor 108 may correspond to wear noise. The media monitor 108 is capable of improving the efficiency with which media can be monitored by inhibiting generation and/or transmission of audio signatures during times when the media monitor 108 suspects the audio sensor may be recording wear noise. Further detail of the media monitor 108 of FIG. 1 is illustrated and described in connection with FIG. 2.

The example network 110 of the illustrated example of FIG. 1 is the Internet. However, the example network 106 may be implemented using any suitable wired and/or wireless network(s) including, for example, one or more data buses, one or more Local Area Networks (LANs), one or more wireless LANs, one or more cellular networks, one or more private networks, one or more public networks, etc. The network 106 enables the media monitor 108 to be in communication with the central facility 112. For example, the media monitor 108 may communicate media monitoring data to the central facility 112. The central facility 112 may communicate data to the media monitor, such as user agreements, or results of media monitoring queries. As used herein, the phrase "in communication," including variances therefore, encompasses direct communication and/or indirect communication through one or more intermediary components and does not require direct physical (e.g., wired) communication and/or constant communication, but rather includes selective communication at periodic or aperiodic intervals, as well as one-time events.

The example central facility 112 of the illustrated example of FIG. 1 collects, aggregates, and/or analyzes media monitoring data from a plurality of media monitoring devices. In the illustrated example of FIG. 1, the central facility 112 accesses audio signatures communicated via the network 110 from the first media monitor 108 and/or the second media monitor 108*b*. The central facility 112 can then perform signature matching to determine identifying information corresponding to media consumed by the first panelist 106*a* and/or the second panelist 106*b*.

Figure 2:
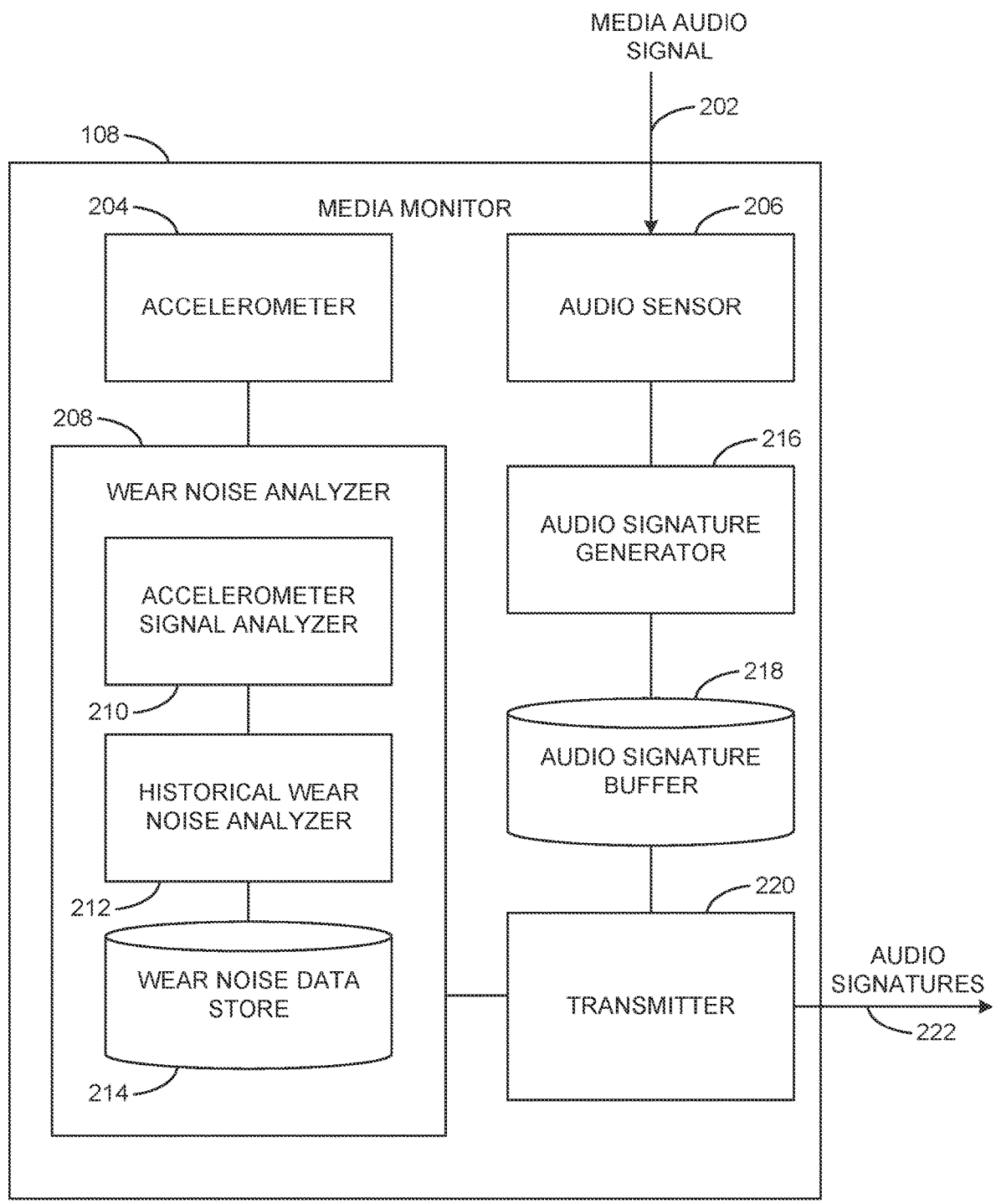
FIG. 2 is a block diagram of an example implementation of the media monitor including wear noise audio signature suppression of FIG. 1.

FIG. 2 is a block diagram of an example media monitor 108 for wear noise audio signature suppression constructed in accordance with the teachings of this disclosure. The example media monitor 108 includes an example accelerometer 204, an example audio sensor 206, an example wear noise analyzer 208, an example accelerometer signal analyzer 210, an example historical wear noise analyzer 212, an example wear noise data store 214, an example audio signature generator 216, an example audio signature buffer 218, and an example transmitter 220.

The accelerometer 204 of the illustrated example of FIG. 2 captures acceleration data and/or other motion data associated with movement of the media monitor 108. In some examples, the accelerometer 204 is separate from the media monitor 108. For example, the accelerometer 204 may be a separate component from the media monitor 108 when both are installed on a wearable device (e.g., a smartwatch). In some examples, the media monitor 108 may determine motion data from another type of sensor (e.g., a gyroscope).

The accelerometer 204 of the illustrated example communicates acceleration data to the wear noise analyzer 208.

The wear noise analyzer 208 of the illustrated example of FIG. 2 analyzes the acceleration data from the accelerometer 204 and determines whether one or more characteristics of the acceleration data satisfy a likelihood of being associated with wear noise. The wear noise analyzer 208 includes an example accelerometer signal analyzer 210, an example historical wear noise analyzer 212, and an example wear noise data store 214.

The accelerometer signal analyzer 210 of the illustrated example of FIG. 2 analyzes data from the accelerometer 204. The accelerometer signal analyzer 210 conducts analysis to determine whether the accelerometer data has characteristics representative of potential wear noise. For example, the accelerometer signal analyzer 210 can determine whether there are fluctuations in the accelerometer signal that exceed a threshold (e.g., since large spikes in acceleration may be associated with the media monitor 108 being in motion). In some examples, the accelerometer signal analyzer 210 determines whether a percent change in the accelerometer data satisfies a threshold. In some examples, the accelerometer signal analyzer 210 communicates an indication as to whether accelerometer data corresponds to wear noise to the audio signature generator 216 to inhibit generation of audio signatures in response to the acceleration data indicating wear noise, and/or the accelerometer signal analyzer 210 communicates with the transmitter 220 to inhibit transmission of the audio signatures 222 in response to the acceleration data indicating wear noise.

The historical wear noise analyzer 212 of the illustrated example of FIG. 2 compares accelerometer data with historical accelerometer data to identify potential wear noise characteristics. For example, the historical wear noise analyzer 212 may compare a portion of the acceleration data received from the accelerometer 204 with an acceleration profile including past data that was identified as wear noise to determine whether the current acceleration data may correspond to wear noise. In some examples, the historical wear noise analyzer 212 determines user-specific characteristics of motion over time. For example, the historical wear noise analyzer 212 may be able to identify when a user is walking or otherwise in motion based on an analysis of accelerometer data over time. In some examples, an initial calibration period may be utilized where a user is instructed to walk for a period (e.g., five minutes), sit for a period as if watching a show (e.g., five minutes), or otherwise perform a certain motion, in order to train the historical wear noise analyzer 212 to identify patterns in acceleration data. In some examples, the historical wear noise analyzer 212 communicates with the audio signature generator 216 to inhibit audio signature generation when the historical wear noise analyzer 212 believes current acceleration data corresponds to wear noise. In some examples, the historical wear noise analyzer 212 communicates with the transmitter to inhibit transmission of the audio signatures 222 when current acceleration data corresponds to wear noise.

The wear noise data store 214 of the illustrated example of FIG. 2 stores wear noise acceleration data. In some examples, the wear noise data store 214 stores all acceleration data (e.g., both acceleration data where wear noise is suspected, and the remaining acceleration data where wear noise is not expected). The historical wear noise analyzer 212 of the illustrated example queries the wear noise data store 214 to determine, based on historical data, whether acceleration data corresponds to wear noise. The wear noise data store 214 may be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., flash memory). The wear noise data store 214 may additionally or alternatively be implemented by one or more double data rate (DDR) memories, such as DDR, DDR2, DDR3, mobile DDR (mDDR), etc. The wear noise data store 214 may additionally or alternatively be implemented by one or more mass storage devices such as hard disk drive(s), compact disk drive(s) digital versatile disk drive(s), etc. While in the illustrated example the wear noise data store 214 is illustrated as a single database, the wear noise data store 214 may be implemented by any number and/or type(s) of databases. Furthermore, the data stored in the wear noise data store 214 may be in any data format such as, for example, binary data, comma delimited data, tab delimited data, structured query language (SQL) structures, etc.

The audio sensor 206 of the illustrated example of FIG. 2 is a microphone. The audio sensor 206 may be any sensor type capable of recording audio signals. The media audio signal 202 is recorded by the audio sensor 206 when a panelist is exposed to the media audio signal and the media monitor 108 is enabled. The audio sensor 206 communicates recording data associated with the media audio signal 202 to the audio signature generator 216. In some examples, the audio sensor 206 is separate from the media monitor 108 but is part of another device (e.g., a wearable device on which the media monitor 108 is installed) and is in communication with the media monitor 108. In some examples, the audio sensor 206 can be disabled in response to the wear noise analyzer 208 detecting accelerometer signal characteristics associated with wear noise.

The audio signature generator 216 of the illustrated example of FIG. 2 generates audio signatures based on data from the audio sensor 206 corresponding to the media audio signal 202 (e.g., based on a recording of the media audio signal 202). In some examples, the audio signature generator 216 can be disabled in response to the wear noise analyzer 208 detecting accelerometer data associated with potential wear noise, to avoid wasting processing resources on generating audio signatures for an audio recording of wear noise. The audio signature generator 216 communicates audio signatures to the audio signature buffer 218 and/or to the transmitter 220.

The audio signature buffer 218 of the illustrated example of FIG. 2 is a storage location for audio signatures generated by the audio signature generator 216. For example, the audio signature generator 216 can communicate audio signatures to the audio signature buffer 218 for storage. The audio signature buffer 218 can serve as a temporary storage location to enable the wear noise analyzer 208 to determine whether wear noise has been detected, and to prevent transmission of any audio signatures that have been generated that may be based on audio of wear noise. In some examples, the audio signature buffer 218 has a designated buffer period for which audio signatures are held before they are communicated to the transmitter 220. In some examples, audio signatures are held in the audio signature buffer 218 until the wear noise analyzer 208 indicates that they can either be transmitted by the transmitter 220 or else discarded (e.g., deleted, marked as corresponding to potential wear noise, etc.).

The example transmitter 220 of the illustrated example of FIG. 2 transmits the audio signatures 222 to the central facility 112 of FIG. 1. The transmitter 220 sends the audio signatures 222 after the wear noise analyzer 208 determines that the audio signatures 222 do not satisfy a likelihood of corresponding to wear noise. In some examples, the transmitter 220 can also receive responses from the central facility 112, such as responses to queries (e.g., to provide media identification feedback to a user). In some examples, the transmitter 220 communicates the audio signatures 222 via the network 110 of FIG. 1. The transmitter 220 may utilize any communications technology, wired or wireless, to communicate the audio signatures 222.

While an example manner of implementing the media monitor 108 of FIG. 1 is illustrated in FIG. 2, one or more of the elements, processes and/or devices illustrated in FIG. 2 may be combined, divided, re-arranged, omitted, eliminated and/or implemented in any other way. Further, the example accelerometer 204, the example audio sensor 206, the example wear noise analyzer 208, the example accelerometer signal analyzer 210, the example historical wear noise analyzer 212, the example wear noise data store 214, the example audio signature generator 216, the example audio signature buffer 218, the example transmitter 220 and/or, more generally, the example media monitor 108 of FIG. 2 may be implemented by hardware, software, firmware and/or any combination of hardware, software and/or firmware. Thus, for example, any of the example accelerometer 204, the example audio sensor 206, the example wear noise analyzer 208, the example accelerometer signal analyzer 210, the example historical wear noise analyzer 212, the example wear noise data store 214, the example audio signature generator 216, the example audio signature buffer 218, the example transmitter 220 and/or, more generally, the example media monitor 108 of FIG. 2 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example accelerometer 204, the example audio sensor 206, the example wear noise analyzer 208, the example accelerometer signal analyzer 210, the example historical wear noise analyzer 212, the example wear noise data store 214, the example audio signature generator 216, the example audio signature buffer 218, the example transmitter 220 and/or, more generally, the example media monitor 108 of FIG. 2 is/are hereby expressly defined to include a non-transitory computer readable storage device or storage disk such as a memory, a digital versatile disk (DVD), a compact disk (CD), a Blu-ray disk, etc. including the software and/or firmware. Further still, the example media monitor 108 of FIG. 2 may include one or more elements, processes and/or devices in addition to, or instead of, those illustrated in FIG. 2, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 3:
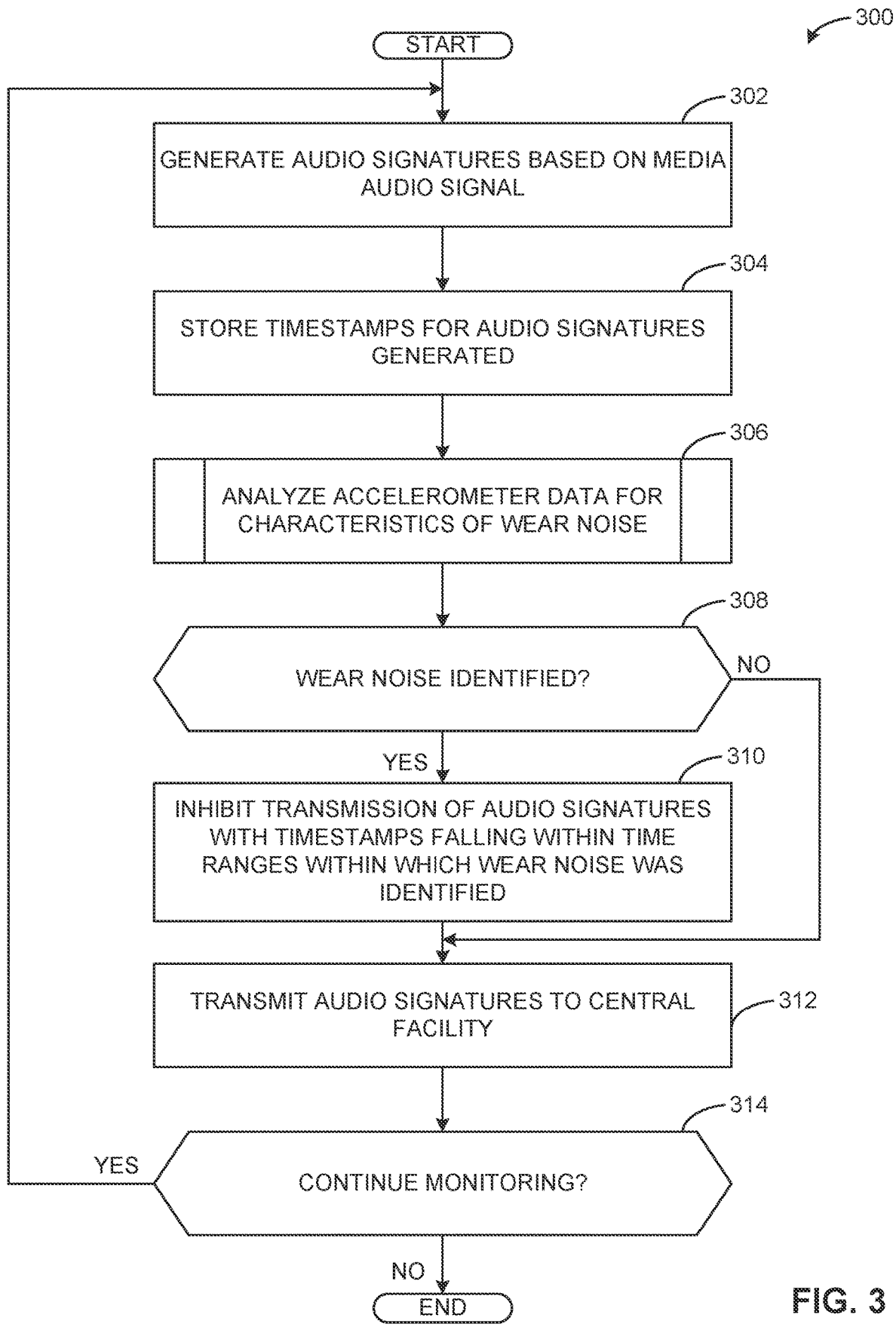
FIG. 3 is a flowchart representative of machine readable instructions that may be executed to implement the media monitor of FIGS. 1 and/or 2 to suppress audio signatures associated with wear noise.
Figure 4:
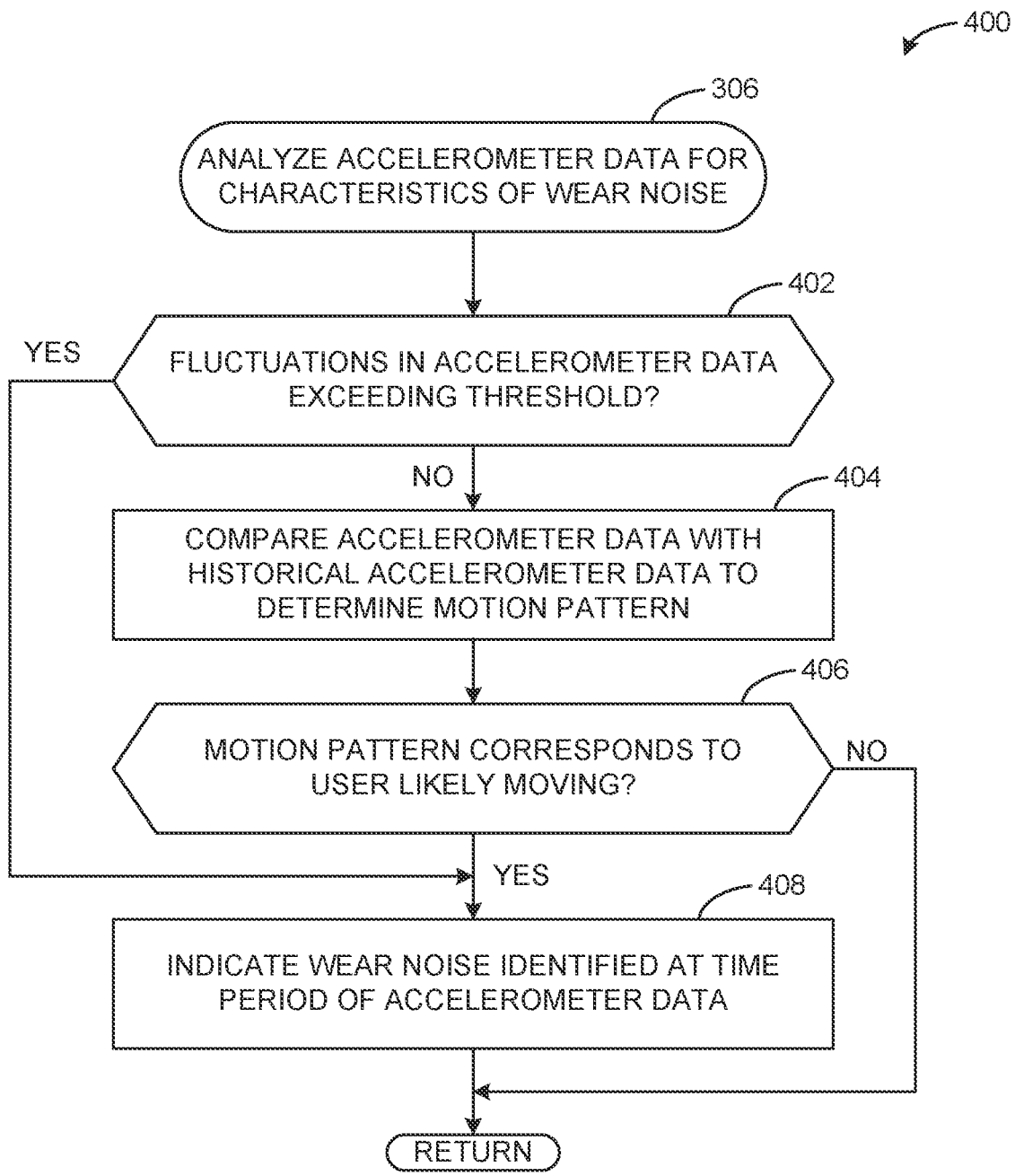
FIG. 4 is a flowchart representative of machine readable instructions that may be executed to implement the media monitor of FIGS. 1 and/or 2 to analyze accelerometer data for characteristics of wear noise.

Flowcharts representative of example hardware logic, machine readable instructions, hardware implemented state machines, and/or any combination thereof for implementing the media monitor 108 of FIG. 2 are shown in FIGS. 3-4.

The machine readable instructions may be one or more executable programs or portion(s) of an executable program for execution by a computer processor such as the processor 512 shown in the example processor platform 500 discussed below in connection with FIG. 5. The program may be embodied in software stored on a non-transitory computer readable storage medium such as a CD-ROM, a floppy disk, a hard drive, a DVD, a Blu-ray disk, or a memory associated with the processor 512, but the entire program and/or parts thereof could alternatively be executed by a device other than the processor 512 and/or embodied in firmware or dedicated hardware. Further, although the example program is described with reference to the flowcharts illustrated in FIGS. 3-4, many other methods of implementing the example media monitor 108 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

The machine readable instructions described herein may be stored in one or more of a compressed format, an encrypted format, a fragmented format, a compiled format, an executable format, a packaged format, etc. Machine readable instructions as described herein may be stored as data (e.g., portions of instructions, code, representations of code, etc.) that may be utilized to create, manufacture, and/or produce machine executable instructions. For example, the machine readable instructions may be fragmented and stored on one or more storage devices and/or computing devices (e.g., servers). The machine readable instructions may require one or more of installation, modification, adaptation, updating, combining, supplementing, configuring, decryption, decompression, unpacking, distribution, reassignment, compilation, etc. in order to make them directly readable, interpretable, and/or executable by a computing device and/or other machine. For example, the machine readable instructions may be stored in multiple parts, which are individually compressed, encrypted, and stored on separate computing devices, wherein the parts when decrypted, decompressed, and combined form a set of executable instructions that implement a program such as that described herein.

In another example, the machine readable instructions may be stored in a state in which they may be read by a computer, but require addition of a library (e.g., a dynamic link library (DLL)), a software development kit (SDK), an application programming interface (API), etc. in order to execute the instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, the disclosed machine readable instructions and/or corresponding program(s) are intended to encompass such machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example processes of FIGS. 3-4 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, and (3) at least one A and at least one B.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

Example machine readable instructions 300 that may be executed by the media monitor 108 of FIGS. 1 and 2 to suppress generation and/or transmission of audio signatures associated with wear noise are illustrated in FIG. 3. With reference to the preceding figures and associated descriptions, the example machine readable instructions 300 of FIG. 3 begin with the media monitor 108 generating audio signatures based on a media audio signal (Block 302). In some examples, the audio signature generator 216 generates audio signatures based on a recording (e.g., or other representation) of the audio signal captured by the audio sensor 206.

At block 304, the media monitor 108 stores timestamps for audio signatures that have been generated. In some examples, the audio signature generator 216 stores timestamps for the audio signatures that have been generated. In some examples, the audio signature generator 216 stores the timestamps in association with the audio signatures stored in the audio signature buffer 218.

At block 306, the media monitor 108 analyzes accelerometer data for characteristics of wear noise. In some examples, the wear noise analyzer 208 analyzes the accelerometer data for characteristics of wear noise. Detailed instructions to analyze the accelerometer data for characteristics of wear noise are illustrated and described in connection with FIG. 4.

At block 308, the media monitor 108 determines whether wear noise has been identified. In some examples, the wear noise analyzer 208 determines whether wear noise has been identified. In response to identifying wear noise, processing transfers to block 310. Conversely, in response to not identifying wear noise, processing transfers to block 312.

At block 310, the media monitor 108 inhibits transmission of audio signatures with timestamps falling within time ranges during which wear noise was identified. In some examples, the wear noise analyzer 208 causes the transmitter 220 to inhibit transmission of audio signatures with timestamps falling within time ranges during which wear noise was identified. In some examples, the wear noise analyzer 208 communicates with the audio signature buffer 218 to cause the audio signatures with timestamps falling within time ranges during which wear noise was identified to be discarded.

At block 312, the media monitor 108 transmits audio signatures to the central facility 112. In some examples, the transmitter 220 transmits the audio signatures 222 to the central facility 112. In some examples, the transmitter 220 transmits the audio signatures 222 to the central facility 112 n response to the wear noise analyzer 208 determining the audio signatures 222 do not correspond, or are not likely to correspond, to wear noise.

At block 314, the media monitor 108 determines whether to continue monitoring. In response to continuing monitoring, processing transfers to block 302. Conversely, in response to not continuing monitoring, processing terminates.

Example machine readable instructions 400 that may be executed by the media monitor 108 to analyze accelerometer data for characteristics of wear noise are illustrated in FIG. 4. With reference to the preceding figures and associated description, the machine readable instructions 400 begin with the media monitor 108 determining whether there are fluctuations in the accelerometer data exceeding a threshold (Block 402). In some examples, the wear noise analyzer 208 determines whether there are fluctuations in the accelerometer data exceeding a threshold. In some examples, the accelerometer signal analyzer 210 determines whether fluctuations in the accelerometer data exceed the threshold. For example, the accelerometer signal analyzer 210 may determine a measure of variance value for a period of accelerometer data to determine whether there are fluctuations in the accelerometer data exceeding a threshold. In response to the fluctuations in accelerometer data exceeding a threshold, processing transfers to block 408. Conversely, in response to there not being fluctuations in the accelerometer data exceeding the threshold, processing transfers to block 404.

At block 404, the media monitor 108 compares accelerometer data with historical accelerometer data to determine a motion pattern. In some examples, the wear noise analyzer 208 compares the accelerometer data with historical accelerometer data to determine a motion pattern. In some examples, the historical wear noise analyzer 212 compares the accelerometer data with historical accelerometer data to determine a motion pattern. For example, the historical wear noise analyzer 212 can determine whether the accelerometer data likely corresponds to a user walking, running or otherwise moving, or sitting.

At block 406, the media monitor 108 determines whether the motion pattern corresponds to the user likely moving. In some examples, the historical wear noise analyzer 212 determines whether the motion pattern corresponds to the user likely moving. In response to the user likely being in motion, processing transfers to block 408. Conversely, in response to the user likely not being in motion, processing returns to the machine readable instructions 300 of FIG. 3 and transfers to block 308.

At block 408, the media monitor 108 indicates that wear noise has been identified at the time period of the accelerometer data. In some examples, the wear noise analyzer 208 indicates that wear noise has been identified at the time period of the accelerometer data during which the wear noise analyzer 208 has determined wear noise has been identified.

Figure 5:
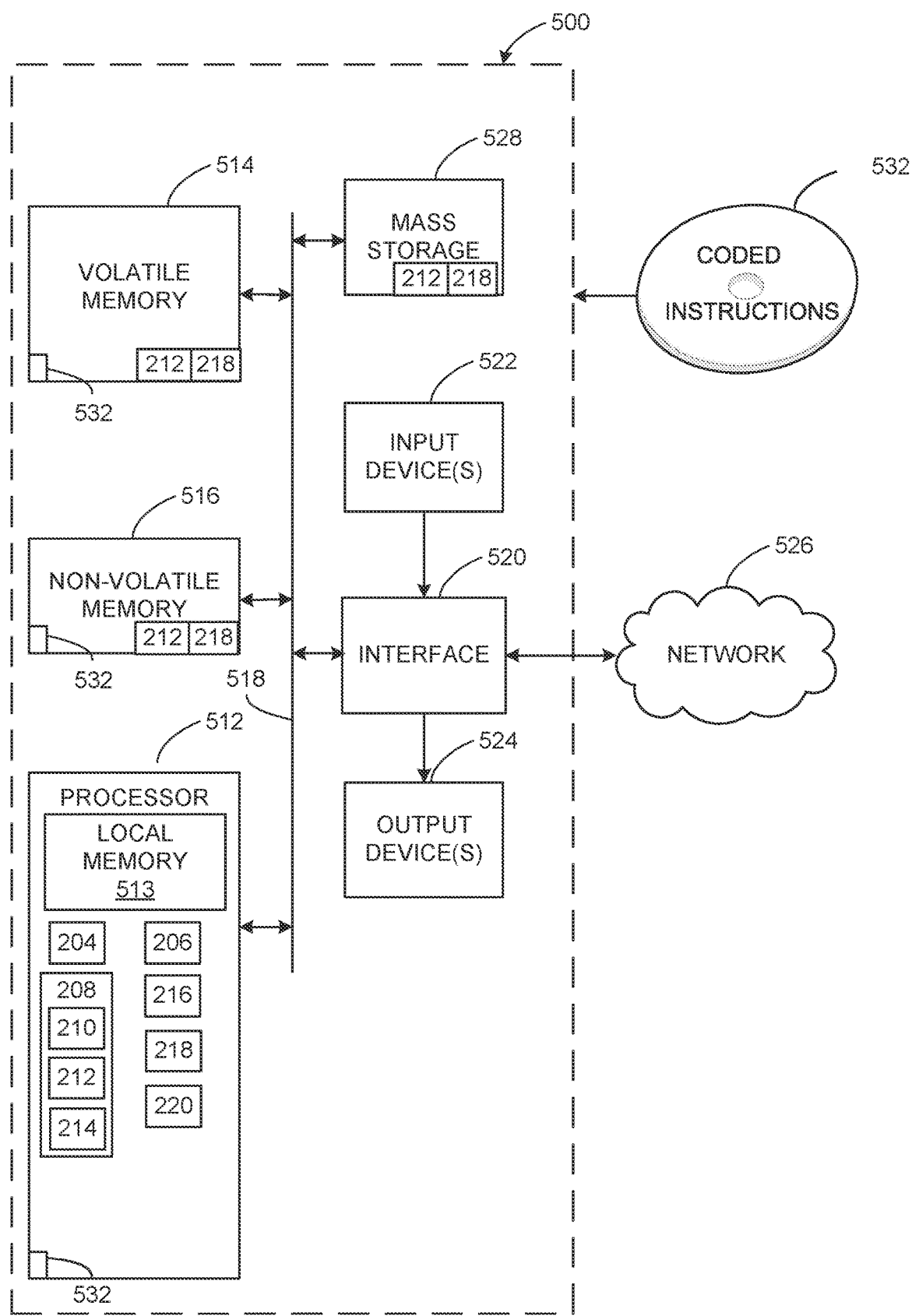
FIG. 5 is a block diagram of an example processing platform structured to execute the machine readable instructions of FIGS. 4-5 to implement the example media monitor of FIGS. 1 and/or 2.

FIG. 5 is a block diagram of an example processor platform 500 structured to execute the instructions of FIGS. 3-4 to implement the media monitor 108 of FIG. 2. The processor platform 500 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, a headset or other wearable device, or any other type of computing device.

The processor platform 500 of the illustrated example includes a processor 512. The processor 512 of the illustrated example is hardware. For example, the processor 512 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the example accelerometer 204, the example audio sensor 206, the example wear noise analyzer 208, the example accelerometer signal analyzer 210, the example historical wear noise analyzer 212, the example wear noise data store 214, the example audio signature generator 216, the example audio signature buffer 218, the example transmitter 220.

The processor 512 of the illustrated example includes a local memory 513 (e.g., a cache). The processor 512 of the illustrated example is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 516 may be implemented by flash memory and/or any other desired type of memory device. Access to the main memory 514, 516 is controlled by a memory controller.

The processor platform 500 of the illustrated example also includes an interface circuit 520. The interface circuit 520 may be implemented by any type of interface standard, such as an Ethernet interface, a universal serial bus (USB), a Bluetooth® interface, a near field communication (NFC) interface, and/or a PCI express interface.

In the illustrated example, one or more input devices 522 are connected to the interface circuit 520. The input device(s) 522 permit(s) a user to enter data and/or commands into the processor 512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 524 are also connected to the interface circuit 520 of the illustrated example. The output devices 524 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 520 of the illustrated example, thus, typically includes a graphics driver card, a graphics driver chip and/or a graphics driver processor.

The interface circuit 520 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 526. The communication can be via, for example, an Ethernet connection, a digital subscriber line (DSL) connection, a telephone line connection, a coaxial cable system, a satellite system, a line-of-site wireless system, a cellular telephone system, etc.

The processor platform 500 of the illustrated example also includes one or more mass storage devices 528 for storing software and/or data. Examples of such mass storage devices 528 include floppy disk drives, hard drive disks, compact disk drives, Blu-ray disk drives, redundant array of independent disks (RAID) systems, and digital versatile disk (DVD) drives.

The machine executable instructions 532, 300, 400 of FIGS. 3-4 may be stored in the mass storage device 528, in the volatile memory 514, in the non-volatile memory 516, and/or on a removable non-transitory computer readable storage medium such as a CD or DVD.

From the foregoing, it will be appreciated that example methods, apparatus and articles of manufacture have been disclosed that enable efficient media monitoring by inhibiting generation and/or transmission of audio signatures when a microphone of the media monitor may have recorded wear noise. The disclosed methods, apparatus and articles of manufacture improve the efficiency of using a computing device by reducing unnecessary processing and transmission of audio signatures that have a high likelihood of not being useful for media monitoring due to the occurrence of wear noise. Further, the disclosed methods, apparatus, and articles of manufacture improve the accuracy with which media monitoring can be performed by only generating and/or transmitting audio signatures for audio recordings that have been determined to not correspond to wear noise. The disclosed methods, apparatus and articles of manufacture are accordingly directed to one or more improvement(s) in the functioning of a computer.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

The following claims are hereby incorporated into this Detailed Description by this reference, with each claim standing on its own as a separate embodiment of the present disclosure.

What is claimed is:

1. An apparatus comprising:
   a wear noise analyzer to determine whether acceleration data corresponds to wear noise having occurred during a first time period, the wear noise analyzer to determine the acceleration data corresponds to wear noise when a change between first acceleration data and second acceleration data exceeds a threshold; and
   a transmitter to inhibit transmission of an audio signature to a central facility in response to the wear noise analyzer determining the acceleration data corresponds to wear noise during the first time period.

2. The apparatus of claim 1, further including an audio signature generator to generate the audio signature based on a media audio signal during the first time period.

3. The apparatus of claim 1, further including an accelerometer to collect the acceleration data during the first time period.

4. The apparatus of claim 1, wherein the wear noise analyzer includes an accelerometer signal analyzer to calculate a variance value to determine the change between the first acceleration data and the second acceleration data, and the accelerometer signal analyzer is to determine whether the variance value exceeds the threshold.

5. The apparatus of claim 1, wherein the wear noise analyzer includes a historical wear noise analyzer to compare the acceleration data to historical acceleration data to determine a motion pattern corresponding to the acceleration data.

6. The apparatus of claim 5, wherein the historical acceleration data includes an acceleration profile for a user that was previously generated and identified as wear noise.

7. The apparatus of claim 6, wherein the wear noise analyzer determines the acceleration data corresponds to wear noise when the historical wear noise analyzer determines the motion pattern matches the acceleration profile for the user.

8. The apparatus of claim 1, wherein the transmitter is to, in response to the wear noise analyzer determining the acceleration data does not correspond to wear noise during the first time period, transmit the audio signature to the central facility.

9. A non-transitory computer readable storage medium comprising instructions that, when executed, cause at least one processor to:
   determine whether acceleration data corresponds to wear noise having occurred during a first time period, the at least one processor to determine the acceleration data corresponds to wear noise when a change between first acceleration data and second acceleration data exceeds a threshold; and inhibit transmission of an audio signature to a central facility in response to determining the acceleration data corresponds to wear noise during the first time period.

10. The non-transitory computer readable storage medium of claim 9, wherein the instructions, when executed, cause the at least one processor to generate the audio signature based on a media audio signal during the first time period.

11. The non-transitory computer readable storage medium of claim 9, wherein the instructions, when executed, cause the at least one processor to calculate a variance value to determine the change between the first acceleration data and the second acceleration data, and the at least one processor is to determine whether the variance value exceeds the threshold.

12. The non-transitory computer readable storage medium of claim 9, wherein the instructions, when executed, cause the at least one processor to compare the acceleration data to historical acceleration data to determine a motion pattern corresponding to the acceleration data.

13. The non-transitory computer readable storage medium of claim 12, wherein the historical acceleration data includes an acceleration profile for a user that was previously generated and identified as wear noise.

14. The non-transitory computer readable storage medium of claim 13, wherein the instructions, when executed, cause the at least one processor to determine the acceleration data corresponds to wear noise when the motion pattern matches the acceleration profile for the user.

15. A method comprising:
determining whether acceleration data corresponds to wear noise having occurred during a first time period when a change between first acceleration data and second acceleration data exceeds a threshold; and in response to determining the acceleration data corresponds to wear noise during the first time period, inhibiting transmission of an audio signature to a central facility.

16. The method of claim 15, further including generating the audio signature based on a media audio signal during the first time period.

17. The method of claim 15, further including:
calculating a variance value to determine the change between the first acceleration data and the second acceleration data; and determining whether the variance value exceeds the threshold.

18. The method of claim 15, further including comparing the acceleration data to historical acceleration data to determine a motion pattern corresponding to the acceleration data.

19. The method of claim 18, wherein the historical acceleration data includes an acceleration profile for a user that was previously generated and identified as wear noise.

20. The method of claim 19, further including determining the acceleration data corresponds to wear noise when the motion pattern matches the acceleration profile for the user.

* * * * *